(12) United States Patent
Singh et al.

(10) Patent No.: US 6,444,458 B1
(45) Date of Patent: Sep. 3, 2002

(54) USE OF TAGETES MINUTA OIL AND ITS COMPONENTS AS ANTIVIRAL AGENTS

(75) Inventors: Bikram Singh; Virendara Prasad Joshi; Raja Ram; Anupama Sharma; Aijaz Asghar Zaidi, all of Himachal Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/765,075

(22) Filed: Jan. 18, 2001

(51) Int. Cl.[7] .................................................. C12N 7/04
(52) U.S. Cl. ........................ 435/238; 424/725; 424/764; 424/408; 504/118
(58) Field of Search ................................ 424/408, 725, 424/764; 435/238; 504/118

(56) References Cited

U.S. PATENT DOCUMENTS 5,662,915 A * 9/1997 Okioga et al.

* cited by examiner

*Primary Examiner*—Leon B. Lankford, Jr.
(74) *Attorney, Agent, or Firm*—Ladas & Parry (57) ABSTRACT

This invention relates to an antiviral composition for the treatment of plant viruses comprising an effective amount of *Tagetes minuta* oil, its active constituents, Z-β-ocimene and dihydrotagetone, or any mixture thereof. The invention also relates to the use of *Tagetes minuta* oil, its active constituents Z-β-ocimene and dihydrotagetone, or any mixture thereof for the treatment of plant viruses.

14 Claims, 10 Drawing Sheets

Fig. 1. Gas Chromatograme of Tagetes Minuta Oil

Fig. 2.   Gas Chromatograme of Acetonitrile Fraction

Fig.3. Gas Chromatograme of Z-β-Ocimene

Fig. 4.  Mass Spectrum of Z-β-Ocimene

Fig. 5.  $^1$H NMR of Z-β-Ocimene

Fig. 6.   ¹³C NMR of Z-β-Ocimene

Fig. 7.  Gas Chromatograme of Dihydrotagetone

Fig. 8   Mass Spectrum of Dihydrotagetone

Fig. 9.   ¹H NMR of Dihydrotagetone

Fig. 10. ¹³C NMR of Dihydrotagetone

USE OF TAGETES MINUTA OIL AND ITS COMPONENTS AS ANTIVIRAL AGENTS

FIELD OF THE INVENTION

The present invention relates to the use of *Tagetes minuta* oil and its components as antiviral agent. More particularly this invention relates to identification of antiviral activity of *Tagetes minuta* oil. This invention also relates to the use of the compounds Z-β-ocimene and dihydrotagetone present in *Tagetes minuta* oil which are now found to inhibit Carnation Ring Spot (CaRSV) and Carnation Vein Mottle Viruses (CaVMV).

BACKGROUND OF THE INVENTION

Carnation Ring Spot (CaRSV) and Carnation Vein Mottle Viruses (CaVMV) are widespread in carnations and cause appreciable amount of damage. Production of disease free plants and chemical control of vectors are the methods employed for reducing disease incidence in the field (Matthews R. E. F. 1991, Plant Virology, Academic Press, San Diego, pp. 835).

Carnation Vein Mottle virus (CaVMV) is a member of potyvirus group, first reported from U.S.A. and is found all over the world (Kissanis B., 1954, Nature 173:1097). On natural hosts chlorotic and darker green spots, flecks and mottling, flower breaking and malformation symptoms are developed after infection. Virus is transmitted mechanically, and also by aphid vectors.

*Chenopodium amranticolor, Chenopodium quinoa* and *Silene pendule* are diagnostically susceptible hosts. On *Chenopodium amaranticolor* chlorotic and necrotic local lesions appear whereas, in *Chenopodium quinoa*, chlorotic lesions with systemic develop after inoculation. *Chenopodium quinoa* and *Dianthus barbatus* are the maintenance and propagation host. It has RNA genone, which is single stranded and virions found in all parts of the host plant. (Morgan J. R., Verhoyen M. and Caneghem, G. V., 1996, Carnation Vein Mottle Potyvirus, In-Viruses of plants, Description and lists from VIDE database ed. Brunt A. A., Crabtree K., Dallwitz M. J., Gibbs A. J. and Watson L. CAB International pp 309–312).

Carnation Ring Spot Virus (CaRSV) first isolated from Dianthus species from U.K. by Kassanis belongs to dianthovirus group (Kassanis B., 1995, Ann. Appl. Biol. 43:103). CaRSV is found all over the world wherever carnations are grown. Virus is transmitted mechanically, and by grafting. Vector transmission is by nematodes. The virus causes leaf mottling, ring spotting, plant stunting, distortion, and flower distortion in host plants whereas, in experimentally infected plants chlorotic and necrotic local lesions, rings and flecks and occasional systemic symptom also appear.

*Chenopodium amaranticolor, Chenopodium quinoa* and *Vigna unguiculata* are local lesion assay hosts. Virus can be maintained on *Dianthus barbatus, Nicotiana clevelandii* and *Phaseolus vulgaris*. Virions are isometric, non-enveloped 34 nm in diameter. Gonome of virus consists of RNA, linear, single stranded. Virions are found in all part of the host plant. (Termaine J. H. and Moran J. R., 1996, Carnation Ring spot virus. In-Viruses of plants, Description and lists for VIDE database ed. Brunt A. A., Crabtree K., Dallwitz M. J., Gibbs A. J., and Watson L. CAB International pp 309–312).

The plant volatile oils have been recognised since antiquity to possess biological activity and a number of plant extracts and pure isolates have been mentioned as containing substances which interfere with or inhibit infection of viruses. Some of the compounds like galangin when used in concentrations ranging form 12–47 µg/ml showed significant antiviral activity against HSV-1 and Cox B1 (Meger J. J. M., Afoloyan A. J., a Taylor M. B., Erasmus D., 1997, Antiviral activity of galangin isolated from the aerial parts of *Helichrysum aureonitens*, J. Ethnopharma, 56:165). Plant *Hyptianthera stricta* L. is used against Encephalitis causing viruses pronounced inhibiting activity 75% and 50% CPE inhibition at 62.5 µg/ml and 15.6 µg/ml against these two viruses (Saxena G., Gupta P., Chandra K., Lakshmi V., 1997, Antiviral activity of *Hyptianthera shivta* L. against encephalitis causing viruses, Indian Drugs, 34:694). The essential oil of *Melaleuca alternifolia* in concentration of 100, 250, 500 ppm was found to be effective in decreasing local lesions of TMV on host plant *Nicotiana glutinosa* (Bishop C. D., 1995, Antiviral activity of the essential oil of *Melaleuca alternifolia* (Maiden & Betche) cheel (Teatree) against Tobacco Mosaic Virus,. J. Essen. Oil Res 7:641). The chemical composition of essential oil for *Senecio graveleopeus* was analysed by GLC-MS and different components like isovaleraldehyde, α-pinene, sabinene, p-cymene, terpinen-4-ol, α and β-eudesmone were identified and found to have antimicrobial activity against *Microccus letus, staphylococus aureus* and antifungal activity against *canidida albicans*. The MIC (Minimum Inhibitory Concentration) was 8.73, 10.91 and $2.13 \times 10^{-2}$ mg/ml respectively against all the three organisms. A number of compounds from different plant extracts have antiviral activity (Perez C., Agnese A. M. Cabrere J. L., 1999, The essential oil of *Senecio graveoleus* (Compositae): chemical composition and antimicrobial activity test 66:91). A new acelycated flavonol glycoside, quercetin exhibited $IC_{50}$ values of 18.1±1.3 µg/ml against HIV integrase (Kim J. H., Woo E. R., Shin C. G., Park 1998, *Acer okamotoanum* and its inhibitory activity against HIV-1 integrase. J. Natural Products 61:145). Three new triterpene lactones lancilactones A, B, C together with the known Kadsulactone A were isolated from stems and roots of *Kadsura lancilimba*. Their structure with sterochemistries was determined- from mass and NMR. Compound 3 inhibited HIV replication with an $EC_{50}$ value of 1.4 mg/ml and a therapeutic index of greater than 71.4 (Chen F. D., Zhang X. S., Wang K. H., Zhang Y. S., Sun Q. Z., Cosentine L. M., and Lee K. H. 1999, Novel Anti-HIV Lancilactone C and related Triterpense from *Kadsura lancilimba* J. Natural Products 62:94). *Salvia fructiosa* essential oil extracted form aerial parts was analysed by GC-MS. It contained 1,8 cineole (eucalyptol) (47.48%) α+β thujone (11.93%) and camphor (9.04%). The essential oil of *S. fuctiosa* and its isolated components; thujone and 1,8 cineole, exhibited activity against 8 bacterial strains. Camphor was almost inactive against 8 bacterial strain. Camphor was almost inactive against all the bacteria tested. The essential oil was almost inactive against all the bacteria tested. The essential oil was bactericidal at 1/4000 dilution; dilutions of upto /1/0000 decreased bacterial growth rates. The essential oil of *S. fructicosa* and its three main components exhibited cytotoxic activity against African Green Monkey Kidney (vero) cells and high levels of virucidal activity against Herpes Simplex Virus 1 (Sivropou A., Nikolaou K. E., Kokkini S. L. and Arsenalics M., 1997, Antimicrobial, cytotoxic and antiviral activities of *Saliva fructicosa* essential oil. Journal of Agriculture and Food chemistry, 45: 3197.) The essential oils and their components exhibited inhibiting properties against viruses (Deans S. G. and Waterman P. G., 1993, Biological activity of volatile oils, in: Volatile oil crops, Hay R. K. M. and Waterman P. G. Longman Scientific and Technical pp. 97) fungi (Baruah P., Sharma R. K. Singh, R.

S. and Ghosh A. C. 1996, Fungicides activity. of some naturally occurring essential oils against *Fusarium monitiform*, Journal of Essen. Oil Res 8:411) bacteria (Chalchal J. C., Garry R. P., Menut C., Lamaty Li., Malhuret R. and Chopineau, J., 1997, correlation between chemical composition and antimicrobial activity VI, Activity of some African essential oils, Journal of Essen. Oil Res. 9:67) malaria (Milnau G., Valentin A., Benoit R., Mallie M., Bastide J. M., 1997, in vitro antimalarial activity of eight essential oils, Journal of Essen. Oil Res. 9:329). These are very few reports on effects of essential oils on viruses or viral infection in either animals or plants.

*Tagetes minuta* L. (Asteraceae) grows wild and yields essential oil having commercial value in perfumery and flavour industry (Handa K. L., Chopra M. M., Nigam M. C., 1963, The Essential Oil Res. 54:372). The essential oil produced from plants has been chemically investigated (Chopra I. C., Nigam M. C., Kapoor C. D. and Handa K. L., 1963, Indian Tagetes Oils, *Soap Perfumes Cosmetics*, 36, 686; Razden T. K., Wanchoo R. K. and Dhar K. L., 1986, Chemical composition and antimicrobial activity of the oil of *Tagetes minuta* L. *Perfum. Kosmet.* 67:52: Villeirs F. J., Garbes C. F. and Lasnvie R. N. 1971, synthesis of tagetones and their occurrence in oil of *Tagetes minuta*, Phytochemistry, 10:1359; Lawrence B. M., Powell R. H., Swith T. M. and Kranes S. W. chemical composition of *Tagetes minuta*, Perf & Flav., Singh B., Sood R. P. and Singh V. 1992, chemical composition of *Tagetes minuta* L. from Himachal Pradesh (India), Jour Essent. Oil Res. 4:525; Thapa R. K., Agrawal S. G., Kalia N. K. and Kapoor R., 1993, Changes in chemical composition of *Tagetes minuta* at various stages of flowering and fruiting, Jour, Essen. Oil Res; 5:375). The oil produced from *Tagetes minuta* was reported to have hypotensive, branchodilatory, spasmolytic, anti-inflammatory and tranquilizing properties (Chandhoke N. and Ghatak B. J. R., 1969, *Tagetes minuta*; Pharmacological action of the essential oil, Indian J. Med Res, 5:864); juvenile hormone mimicking activity (Saxena B. P. and Srivastava J. B., 1973, juvenile hormone mimicking substances, Indian J. Exp. Biol, 11:56) 5-E Ocimenone was reported to exhibit mosquito larvaecideal activity (Maradufu A., Lubega R. and Dorn F., 1978, Isolation of 5-E-ocimenone, A mosquito larvicides from *Tagetes minuta*. J. Natu.Prod.41:183).

So far only synthetic compounds have been used against plant viruses. Ribavirin (Virazole) (Lozoya-Saldana H., Dawson O. and Murashige T., 1984, Effect or ribavirin and adenine arabinoside on tobacco mosaic virus in *Nicotiana tabacum* L. var. *xanthim* tissue cultures. Plant Cell Tissue Org. Cult., 3:41). Tiazofurin (Caner J., Amelia V. and Vicente M., 1984, Effect of tiazofurin on tomato plants infected with tomato spotted wilt virus. Antiviral Res., 4:325) and Pyrazofurin (Lerch B., 1987, on inhibition of plant virus multiplication by ribavirin, Antiviral Res., 7:257). Synthetic compounds which inhibit virus replication are found to be effective against at least 16 plant viruses (Hansen A. J. 1989, Antiviral chemicals for plant disease control, Critical Review in Plant Sciences, 8: (1) 45). Approximately 1000 ppm ribavirin are needed to inhibit local lesion development and to prevent infection with susceptible viruses such as PVX. In callus culture, PVX was not inhibited by 100 ppm ribavirin in the medium. However, when these calli started to differentiate, 10 ppm were enough to prevent virus spread into 90% of developing shoots.

PNRSV seems to be resistant to ribavirin (Hansen A. J. 1984, Effect of ribavirin on green ring mottle saucan agent and necrotic rings spot virus in Prumus species, Plant Dis. Rep. 68:216) and TMV is much less susceptible than other viruses, except during the very early replicative steps directly following inoculation (Dawson O. and Lozoya—Saldana H., 1984, Examination of niode of action of ribavirin against tobacco mosaic virus. Intervirology, 22:77) Ribavirin is relatively or completely ineffective against BGMV, SSV and CaMV (Kluge S. and Ortel C., Arch 1976, Priufung von virazol auf vermehrung des gurkenmosaik-virus (cucumber mosaic virus) und des nelken scheckungs-virus (carnation mottle virus) *Phytopathoi. Pflanzenschutz*, 14:219; Caner J., Amelia V., and Vicente M. 1984, Effect of tiazofurin on tomato plants infected with tomato sported wilt virus. Antiviral Res., 4:325). In some reports, tiazofurin (Lerch B., 1987, on the inhibition of plant virus multiplication by ribavirin Antiviral Res., 7:257) and Pyrazofurin are tested to see antiviral effect on a range of plant viruses. Other synthetic antivirals are purine-based analogs 8'-azaguanine (Matthews R. E. F., 1954 Effects of some purine analogues on tobacco mosaic virus. J. Gen Microbiol 10:521), adenine arabinoside. (Lozoya—Saldana H. and Dawson W. O. Rev. Mex. 1986, Effect de ribavirin adenina arabinosida sorbre el virus mosaico del tabac el virus moteado clorotico del chicaro de vace in vivo. *Fitopatrol*. 3:38, 1985, Rev. Plant Pathol 65:306) Uracils (Commoner B. and Mercer F. L. 1951, Inhibition of biosynthesis of tobacco mosaic virus by thiouracil, *Nature* (London), 168:113) 5-Azauracil (Cassells A. C. and Long R. D. 1982, The elimination of potato viruses X, Y. S and M in meristen and explant cultures of potato in presence of virazole, Potato Res., 25:165) and other large number of cyclic compounds and non-cyclic azyne compounds (Schuster G., Heinisch L., Schulze W., Ulbright H. and Willitzer H., 1984, Antiphytovirole verbindungen mit nich and zyklischer Azin-struktur Phytopathol. Z 111:97).

Some plant extracts have also been screened for their antiviral activity but these extracts have not been exploited commercially. Only a few reports are available in which essential oils were used as antiviral agent. Most of this work done on Tobacco mosaic virus (Bishop C. D, 1995. Antiviral activity of essential oil of *Melaleuca alternifolia* (Maidan & Betche) cheel (Tea tree) against tobacco mosaic virus. J. of Essen Oil Res., 1995 7:6,641).

The essential oil of *Melaleuca alternifolia* (100, 250 or 500 ppm) was sprayed on plants of *Nicotiana glutinosa* inoculated before plants were inoculated with tobacco mosaic virus isolated form infected tomato leaves. The essential oil treatment reduced lesion number for at least 10 days post inoculation. (Rao G. P., Pandey A. K., Shukla K., 1986, Essential oils of some higher plants vis-a-vis some legume viruses. Indian perfumer 30:4, 483–486). Essential oils of *Ageratum conyzoides, Callistemon lanceolatus (C.citrinus), Carum copticum (Trachyspermum ammi) Ocimum sanctum* and *Peperomia pellucida* were evaluated for inhibitory activity against cowpea mosaic virus (CPMV), mung bean mosaic virus (MBMV), bean commonil mosaic virus (BCMV) and southern bean mosaic virus (SBMV). *Ocimum sanctum* at 3000 ppm gave the best inhibition of 89.6, 90, 92.7, 88.2% against CMV, MBMV, BCMV, and SBMV respectively. The other oils also showed inhibitory activity against other viruses.

Another report showed 62% inhibition against tobacco mosaic virus. The fresh hydrodistilled carrot leaves yielded 0.07% essential oil, analysed by GLC and TLC. Constituents were identified by IR, NMR and mass spectra. Antifungal activity was tested against *Colletotrichum capsici* and *Sclerotium rolfsii*, antibacterial activity tested against *E. Coli* and Aeromonas sp. and antiviral activity against tobacco mosaic tobamovirus. Twenty nine compounds were identified and the major constituents were Sabinene (10.93%) linalool (14.90%), linalyl acetate (8.35%), Carvone (8.77%) of C. caprici and S. folfric by 3–6% and 80% respectively. Aeromonas sp. and E. coli were inhibited at 20% and 16% respectively (Khanna R. K., Sharma O. S., Singh A., Battacharya S. C., Sen N., Sethi K. L. 1989, The essential oil from leaves of Dacus carota Linn. Var Sativa. Proceedings of 11th International Congress of essential oils, fragrances and flavours. New Delhi India, Nov. 12–16, 1989 Vol 4 Chemistry analysis and structure 1990, 173–176).

Tagetes minuta oil was found to be active against carnation ring spot (CaRSV) and carnation vein mottle viruses (CaVMV). The ingredients present in the oil namely dihydrotagetone and ocimene when tested individually in pure form, were found to have enhanced antiviral activity against two carnation viruses. The oil as such and the bioactive consitituent present in oil can be commercially used as an natural and eco-friendly antiviral products.

After application of whole oil of Tagetes minuta and its compounds (ocimene and dihydrotagetone) individually for antiviral activity for two carnation viruses i.e. CaVMV and CaRSV following results were observed. In case of whole oil which is applied on the half leaf of the host plant Chenopodium amaranticolor in comparison to control (Virus+Buffer only) applied on other half of leaf, number of lesions were observed. Each concentration of whole Tagetes minuta oil and its pure isolated components were applied on 10 leaves so that the average could be taken.

Objects of the invention

The main object of the present investigation is to evaluate the antiviral activity of Tagetes minuta oil.

Another object of the present invention is to isolate and characterize antiviral components from Tagetes minuta oil.

Still another object of the present invention is to provide easy and convenient method to enrich Z-β-ocimene and dihydrotagetone from the tagetes oil by solvent-solvent partitioning.

Yet another object of the present investigation is to provide control measure for carnation and for other plant viruses using natural products.

Yet another object of the present investigation is to provide quick and efficient natural products to control Poty and Diantho group viral infection.

SUMMARY OF THE INVENTION

Accordingly the present investigation provides identification of antiviral activity of Tagetes minuta oil and its components which comprises of (a) Hydrodistillation of Tagetes oil (b) drying and storage of oil (c) fractionating the oil into the hydrocarbon rich fraction and ketone rich fraction by solvent—solvent partitioning (d) Isolation of dihydrotagetone and ocimene by chromatographic techniques (e) Raising of host plant (f) Application of whole oil and pure isolates in ppm concentration on leaves of Chenopodium amaranticolor.

In an embodiment of the present invention Tagetes minuta oil was obtained by hydro/steam distillation in laboratory/pilot scale.

In another embodiment of the present invention the two major constituents ocimene and dihydrotagetone were enriched in the oil by solvent—solvent partitioning.

In yet another embodiment of the present invention, Tagetes minuta oil was tested against two carnation viruses.

In yet another embodiment of the present invention, dihydrotagetone was tested against two carnation viruses.

In yet another embodiments of the present invention, ocimene was tested against two carnation viruses.

DETAILED DESCRIPTION OF THE INVENTION

The essential oil of Tagetes minuta was produced by steam distillation in pilot plant or by hydrodistillation on Clevenger type apparatus (Clevenger J. F. 1928, J. Amer Pharm Assoc. 17:346) when the crop is matured generally during the month of Sept–Dec (India). Drying of the oil is generally done in anhydrous sodium sulphate or sodium chloride. The oil may be stored in aluminium containers or in amber coloured glass bottles, without leaving any gap of foreign particles. The freshly distilled Tagetes minuta oil contains ocimene 54.97%, and dihydrotegetone 32.58% 9Singh B., Sood R. P. and Singh V., 1992, chemical composition of Tagetes minuta oil from Himachal Pradesh (India) J; Essent. Oil Res. 4:1992).

For enrichment of two major constituents present in tagetes oil, primary fractionation of hydrocarbons and ketones (ocimene and dihydrtotagetone), it is subject to solvent—solvent partitioning using n-pentane n-hexane may also be used and acetonitrile. Final purification of these components is achieved by chromatographic separation using Silica gel (60–120 mesh). The purity of the compounds was checked with the help of TCL and GC. Other components, tagetones and ocimenones could not be isolated in pure form because these components get polymerise at faster rate.

The whole oil of Tagetes minuta and its pure components i.e. ocimene and dihydrotagetone were tested individually with virus cultures of CaVMV and CaRSV and applied on the leaves of Chenopodium amaranticolor. In all the experiments each concentration of three testing mixtures were applied on ten leaves of Chenopodium amaranticolor plant. The isolated compounds were stored at 0° C. for two months and the experiments were repeated.

EXAMPLE 1

Figure 1:
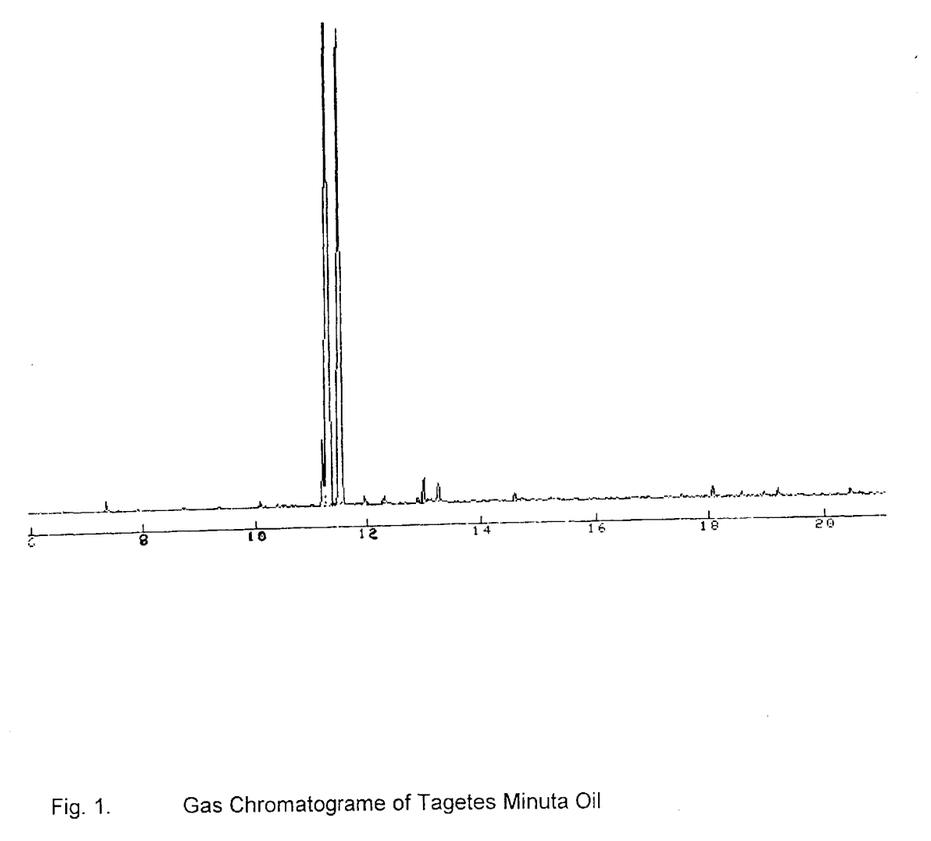
FIG. 1 is a gas chromatogram of Tagetes minuta oil.
Figure 2:
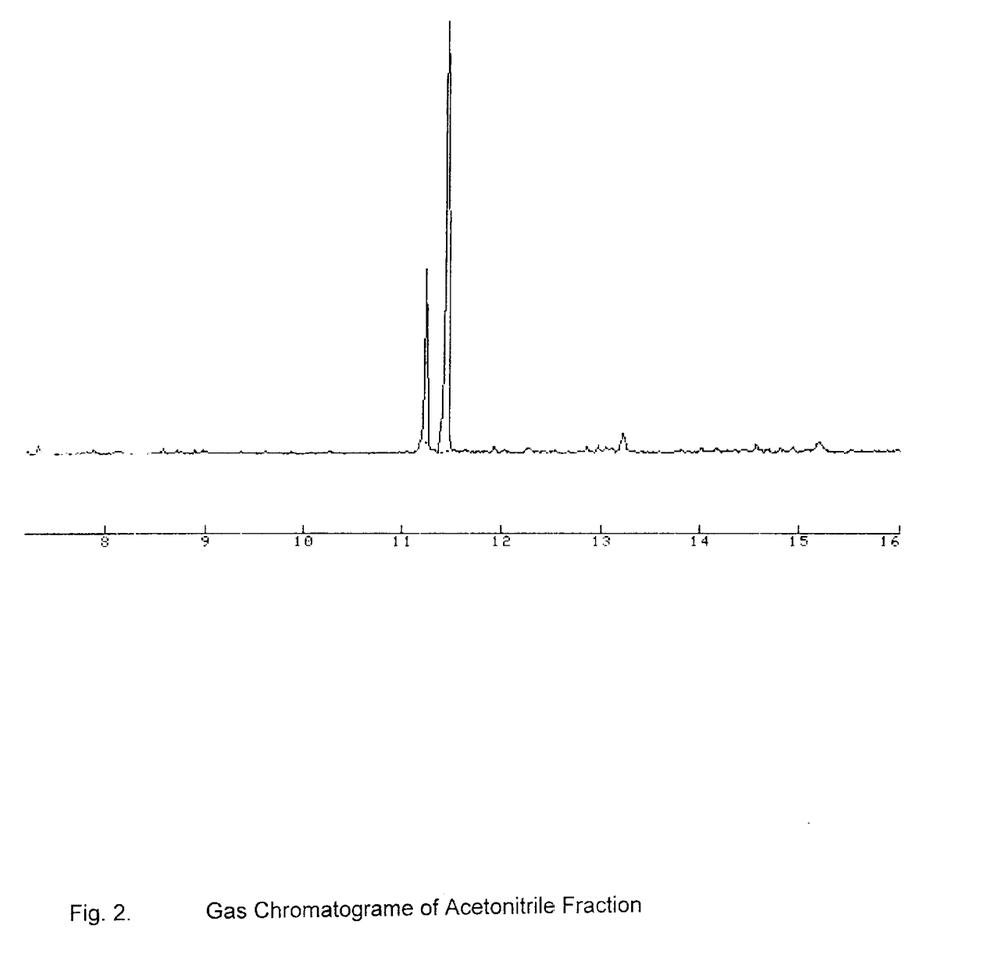
FIG. 2 is a gas chromatogram of the acetonitrile fraction.
Figure 3:
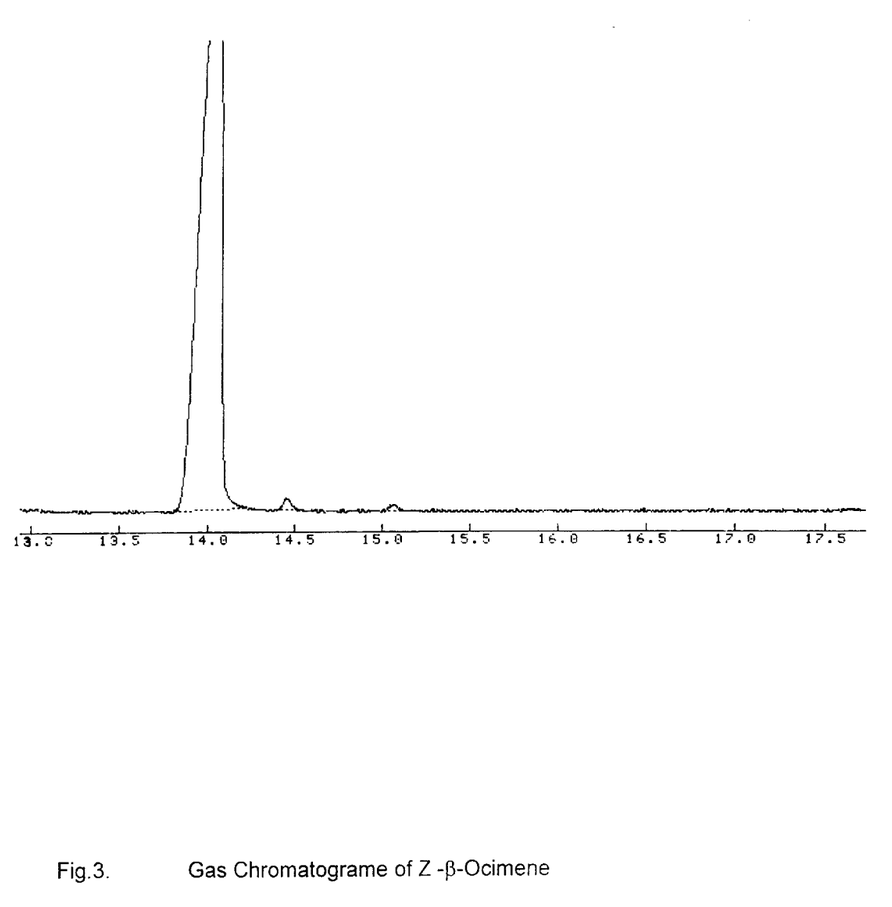
FIG. 3 is a gas chromatogram of Z-β-ocimene.
Figure 4:
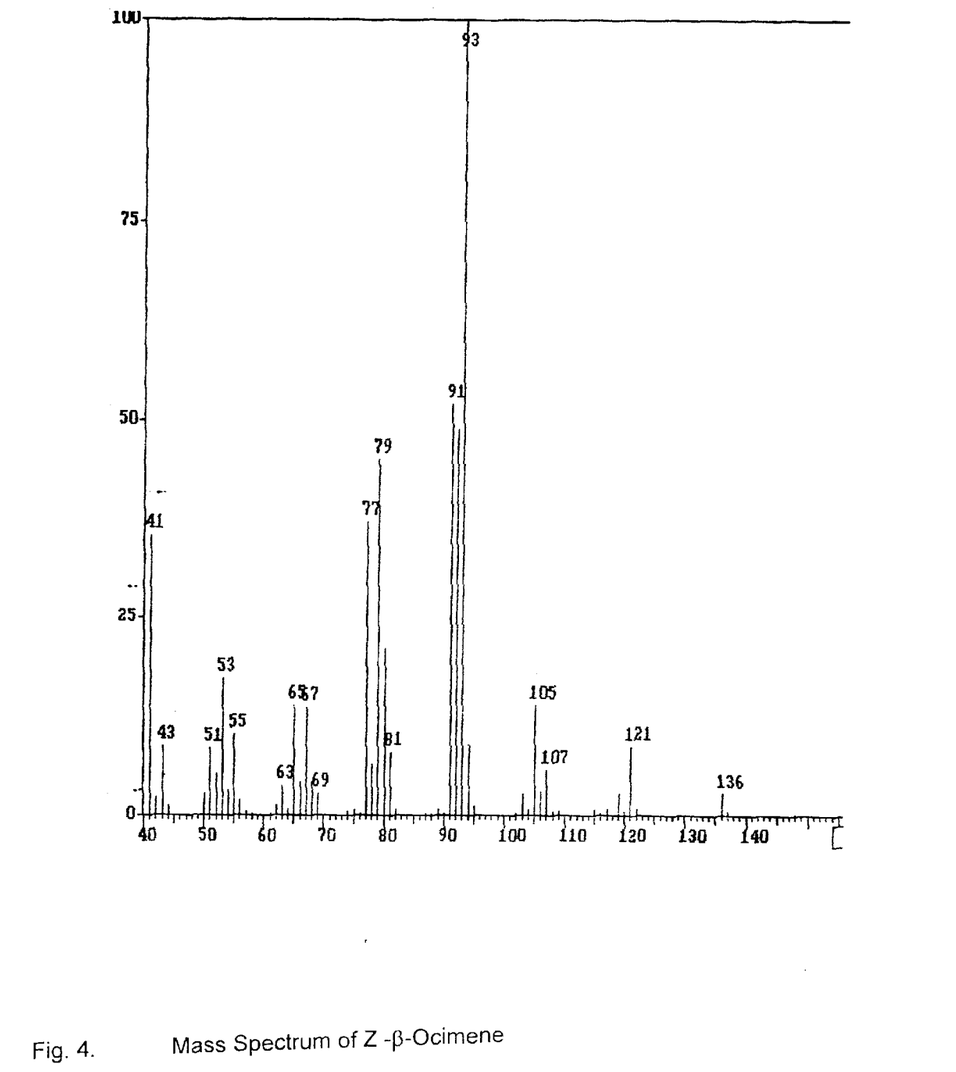
FIG. 4 is a mass spectrum representation of Z-β-ocimene.
Figure 5:
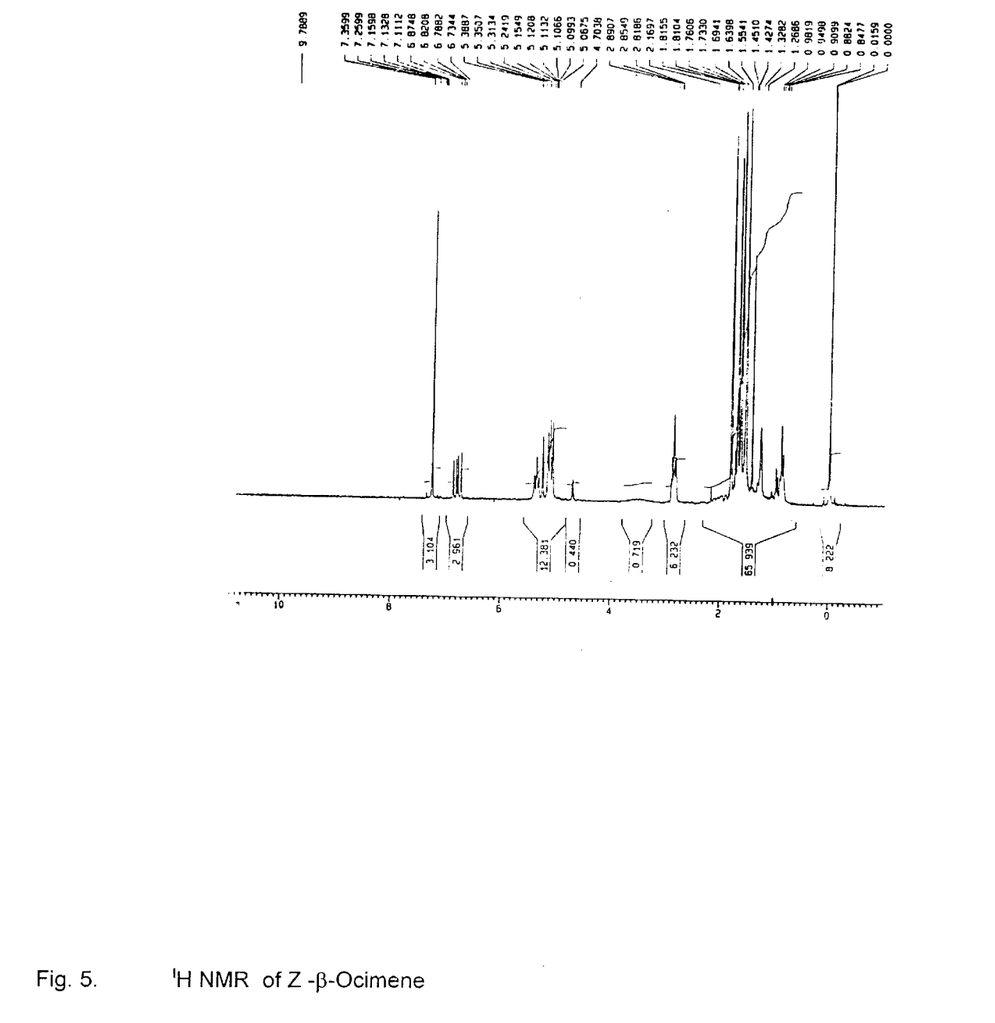
FIG. 5 is the $^1$H NMR of Z-β-ocimene.
Figure 6:
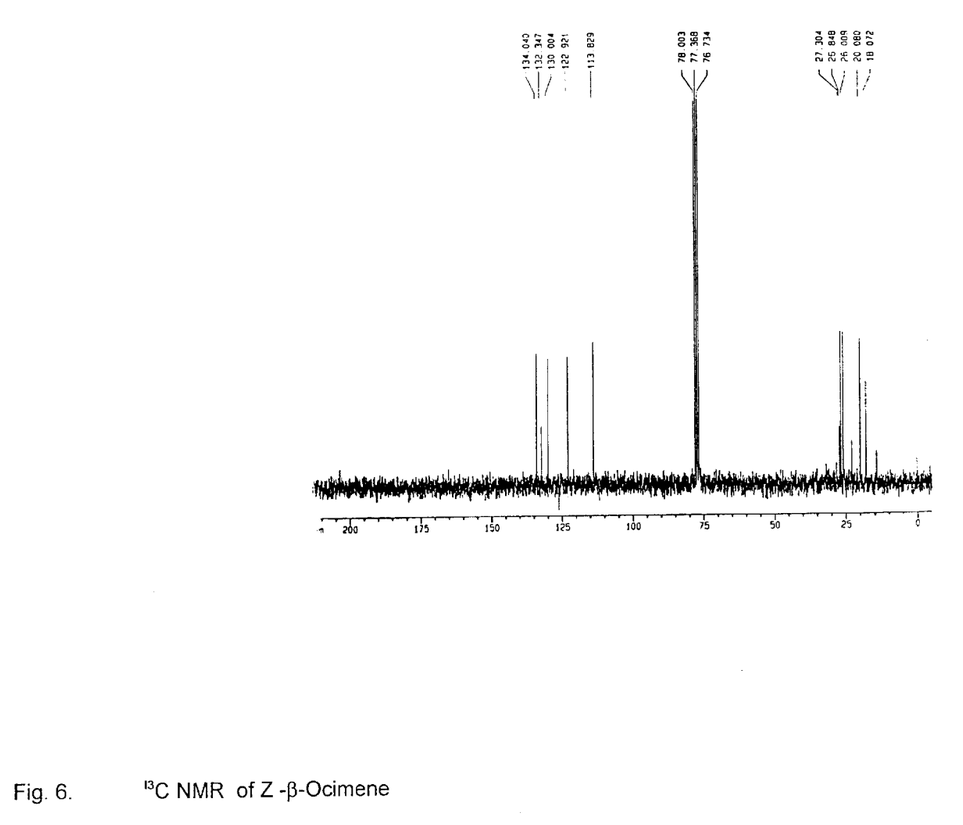
FIG. 6 is the $^{13}$C NMR of Z-β-ocimene.

In 350 ml of Tagetes minuta oil, 250 ml of acetonitrile and 250 ml of n-pentane (may be replaced by n-hexane or n-heptane) were added and mixture was shaken slowly in separating funnel. This was allowed to stand for half an hour. After separating two layers, the acetonitrile layer was washed three times with n-pentane (250 ml each), the pentane fractions were combined and the solvent evaporated i.e. n-pentane from pentane fraction and acetonitrile form acetonitrile fraction. After analysing both the fractions by Gas Chromatographic technique, following percentage of ocimene (hydrocarbon) and dihydrotagetone (ketone) were observed. The freshly distilled *Tagetes minuta* oil contained ocimene 54.97% and dihydrotagetone 32.58%.
1. Pentane fraction : Ocimene 62.5% Dihydrotagetone 24.62%
2. Acetonitrile Fraction Ocimene 26.96% Dihydrotagetone 69.87%

The enrichment of dihydrotagetone was achieved form 32.5%, present in freshly distilled oil to nearly 70% after partitioning.

Figure 7:
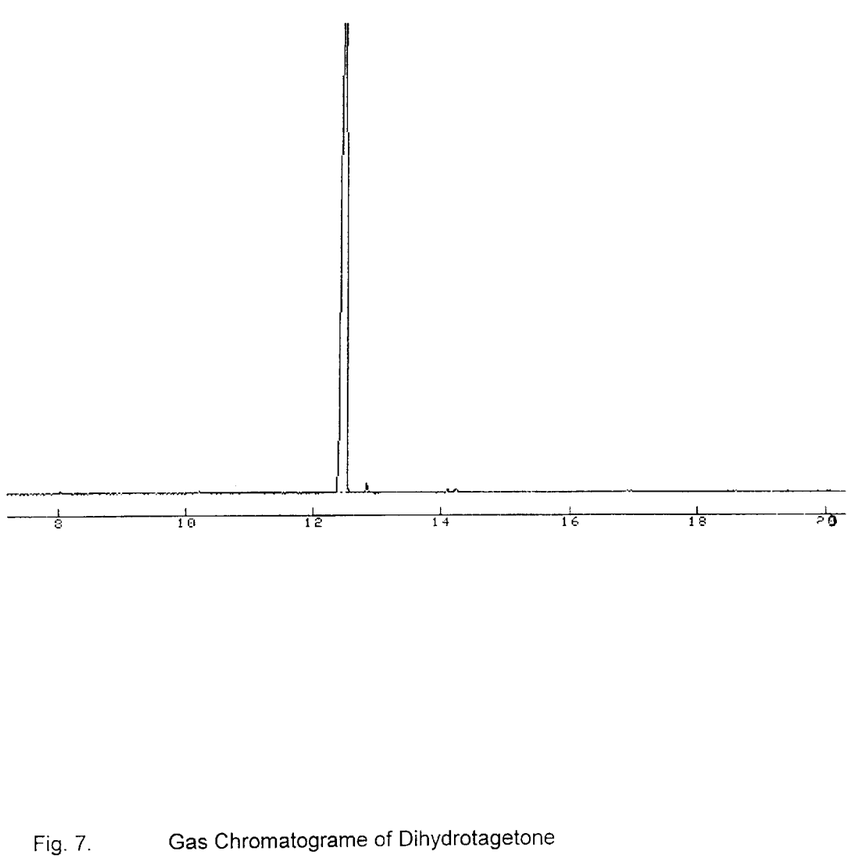
FIG. 7 is the gas chromatogram of dihydrotagetone.
Figure 8:
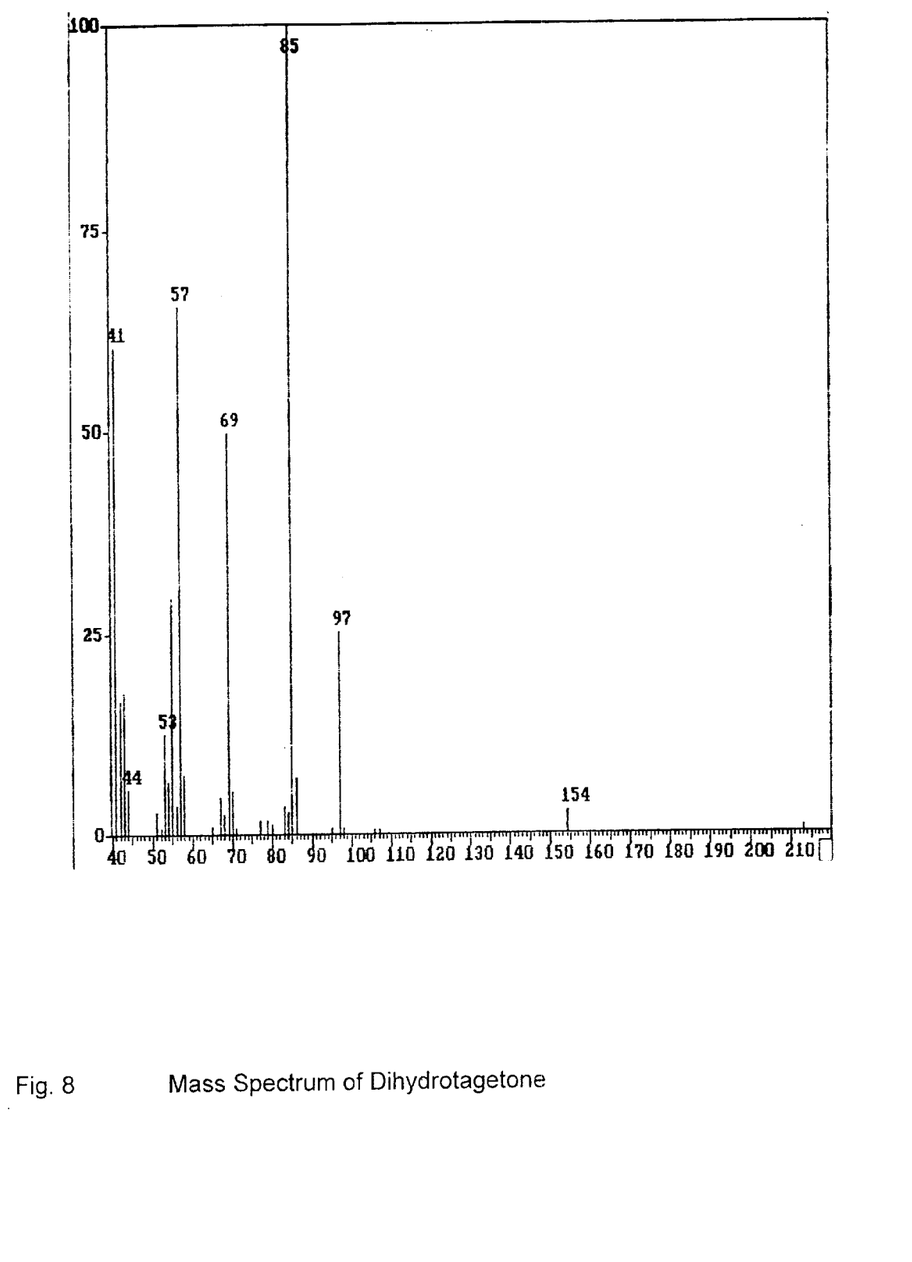
FIG. 8 is the mass spectrum representation of dihydrotagetone.
Figure 9:
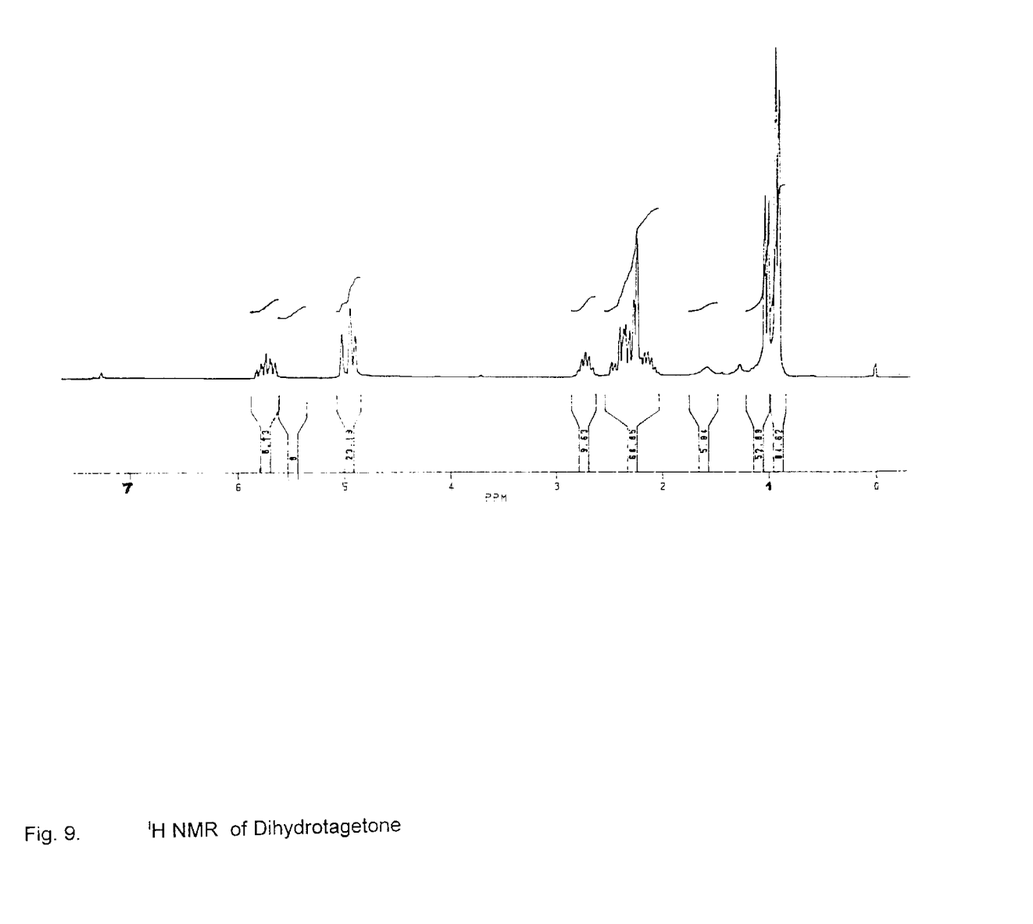
FIG. 9 is the $^1$H NMR of dihydrotagetone.
Figure 10:
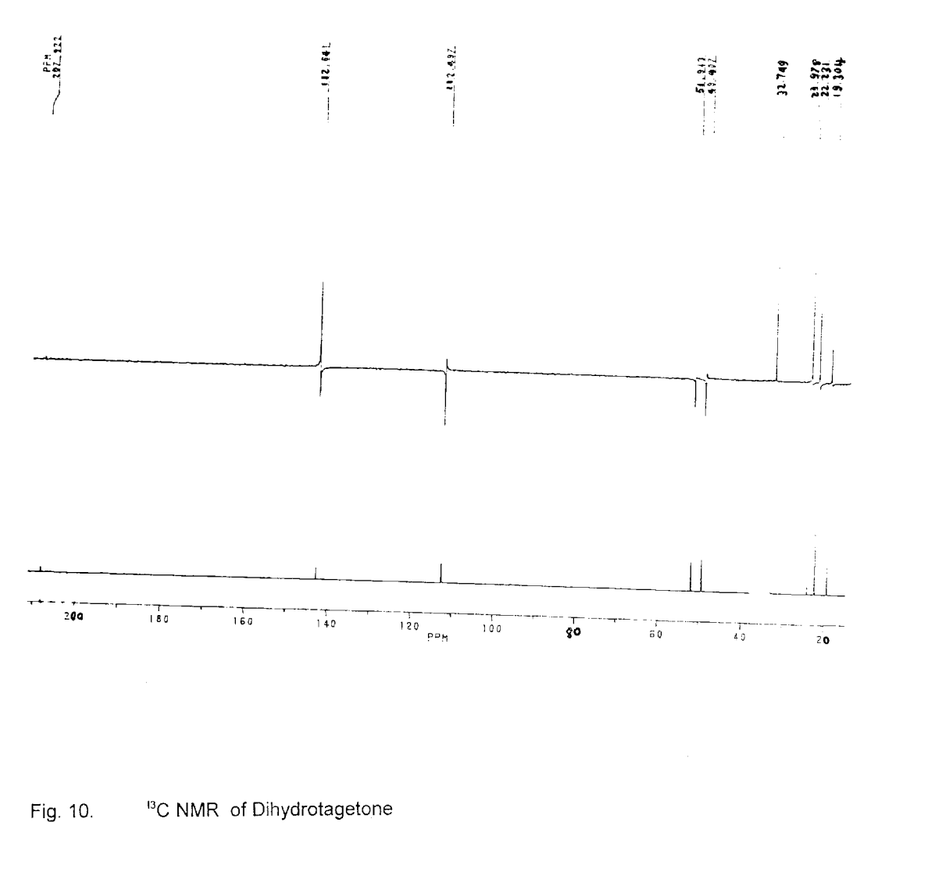
FIG. 10 is the $^{13}$C NMR of dihydrotagetone.

The acetonitrile fraction was subjected to the column chromatography on Silica gel (60–120 mesh), run initially with n-hexane and then with an increasing polarity with ethyl acetate upto 2% to get pure dihydrotagetone. Confirmation of dihydrotagetone was made by various analytical techniques like IR, GC, GC-MS, $^1$H & $^{13}$C NMR spectroscopy and the odour profile was checked by the internal faculty members.

Identification

The identification and structure confirmation was done with the help of MS, IR, $^1$H-NMR and $^{13}$C-NMR

| | Dihydrotagetone |
|---|---|
| Molecular Formula | $C_{10}H_{18}O$ |
| m/e (%) | 154 (10), 97 (30), 85 (100), 69 (50) |
| | 57 (65), 55 (35), 53 (18), 44 (15), 41 (60) |
| $^1$H-NMR (ppm, CDCl$_3$) | 4.89–5.02 (2H, m, H-1), 5.64–5.78 (1H, m, H-2) 2.68–2.75 (1H, m H-3), 2.09–2.47 (4H, m, H-4, 6) 1.11–1.26 (3H, d J= 6 Hz, H-8), 1.02–0.89 (6H, d, J= 6 Hz, H-9, 10) |
| $^{13}$C-NMR(ppm, CDCl$_3$) | 112.49, (C-1), 142.64 (C-2), 23.97 (C-3), 207.9 (C-4), 51.94 (C-5), 49.4 (C-6) 32.75 (C-7), 32.75 (C-7), 22.23 (C-8) 19.8 (C-9), 22.23 (C-10). |
| | Ocimene |
| Molecular Formula | $C_{10}H_{16}$ |
| m/e (%) | 136 (5), 121 (15), 1.5 (19), 93 (100), 91 (52), 79 (45), 65 (15), 53 (20), 41 (27) |
| $^1$H-NMR (ppm, CDCl$_3$) | 1.55, (3H, s, H-8), 1.63 (3H,s, H-10), 1.81 (3H, s, H-9), 2.85 (2H, t, J=7.5 Hz, H-5), 5.06–5.38 (4H, m, H-1, 4, 6), 6.73–6.87 (1H, m, H-2). |
| $^{13}$C-NMR(ppm, CDCl$_3$) | 113.83 (C-1), 134.04 (C-2), 132.34 (C-3) 130.0 (C-4), 26.85 (C-5, 122.92 (C-6) 132.34 (C-7), 18.07 (C-8) 26.03 (C-9) 20.09 (C-10) |

EXAMPLE 2

Virus Culture

The Cultures of Carnation ring spot and Carnation vein motto viruses were maintained both in natural host and on *Phaseolus vulgaris* and *Chenopodium quinoa* which are maintenance and propagation host of these viruses respectively. For virus culture, leaves of fifteen days old individual virus inoculated host plants with CaVMV and CaRSV were ground in phosphate buffer pH 7.5 and the viruses were extracted separately in crude sap.

Screening of Antiviral Activity

Activity of the above volatile oils were tested against Carnation ring spot and Carnation vein mottle virus in different dilutions. Most of the tests were performed by using 0.5% and 2.5% concentration of essential oils as the phytotoxic effect appeared on *Chenopodium amaranticolor* leaves, at higher concentrations. The 0.5% and 2.5% concentration of essential oils were mixed with crude sap containing each virus and incubated at room temperature for 24 hrs. After incubation, sap containing virus were inoculated individually on bioassay host *Chenopodium amaranticolor* after adding Cellite (as abrasive) to monitor the inhibitory effect. Following results were obtained in different concentrations.

TABLE 1a

Treatment of CaVMV with 0.5% *Tagetes minuta* oil

| | No. of Lesions on | | Average No. of lesions | | |
|---|---|---|---|---|---|
| S.No. | Test | Control | Test | Control | % inhibition |
| 1 | 39 | 713 | 3.9 | 71.1 | 94.5 |
| 2. | 46 | 657 | 4.6 | 65.7 | 92.2 |
| 3. | 42 | 702 | 4.2 | 70.2 | 94.2 |

TABLE 1b

Treatment of CaRSV with 0.5% *Tagetes minuta* oil

| | No. of Lesions on | | Average No. of lesions | | |
|---|---|---|---|---|---|
| S.No. | Test | Control | Test | Control | % inhibition |
| 1 | 67 | 761 | 6.7 | 76.1 | 91.3 |
| 2. | 55 | 769 | 5.5 | 76.9 | 92.8 |
| 3. | 65 | 770 | 6.5 | 77 | 91.5 |

TABLE 2a

Treatment of CaVMV with 2.5% *Tagetes minuta* oil

| | No. of Lesions on | | Average No. of lesions | | |
|---|---|---|---|---|---|
| S.No. | Test | Control | Test | Control | % inhibition |
| 1 | 82 | 699 | 8.2 | 69.9 | 88.2 |
| 2. | 76 | 648 | 7.6 | 64.8 | 88.2 |
| 3. | 70 | 655 | 7.0 | 65.5 | 89.3 |

TABLE 2b

Treatment of CaRSV with 2.5% *Tagetes minuta* oil

| | No. of Lesions on | | Average No. of lesions | | |
|---|---|---|---|---|---|
| S.No. | Test | Control | Test | Control | % inhibition |
| 1 | 73 | 582 | 7.3 | 58.2 | 87.45 |
| 2. | 77 | 624 | 7.7 | 62.4 | 87.6 |
| 3. | 75 | 612 | 7.5 | 61.2 | 87.7 |

TABLE 3a

Treatment of CaVMV with 0.5% Dihydrotagetone

| | No. of Lesions on | | Average No. of lesions | | |
|---|---|---|---|---|---|
| S.No. | Test | Control | Test | Control | % inhibition |
| 1 | 38 | 141 | 4.22 | 15.66 | 73.04 |
| 2. | 40 | 150 | 4.44 | 15.66 | 73.3 |
| 3. | 45 | 152 | 5.00 | 15.70 | 70.3 |

TABLE 3b

Treatment of CaRSV with 0.5% Dihydrotagetone

| | No. of Lesions on | | Average No. of lesions | | |
|---|---|---|---|---|---|
| S.No. | Test | Control | Test | Control | % inhibition |
| 1 | 32 | 115 | 4.22 | 15.66 | 72.1 |
| 2. | 41 | 141 | 4.44 | 15.66 | 70.9 |
| 3. | 42 | 150 | 5.00 | 15.70 | 72.0 |

TABLE 4a

Treatment of CaVMV with 2.5% Dihydrotagetone

| | No. of Lesions on | | Average No. of lesions | | |
|---|---|---|---|---|---|
| S.No. | Test | Control | Test | Control | % inhibition |
| 1 | 31 | 183 | 3.44 | 20.33 | 83.0 |
| 2. | 25 | 192 | 2.77 | 21.33 | 87.0 |
| 3. | 38 | 200 | 4.20 | 22.22 | 81.0 |

TABLE 4b

Treatment or CaRSV with 2.5% Dihydrotagetone

| | No. of Lesions on | | Average No. of lesions | | |
|---|---|---|---|---|---|
| S.No. | Test | Control | Test | Control | % inhibition |
| 1 | 82 | 155 | 2.8 | 15.5 | 81.8 |
| 2. | 25 | 140 | 2.5 | 14.0 | 82.0 |
| 3. | 40 | 195 | 4.0 | 19.5 | 79.4 |

TABLE 5a

Treatment of CaVMV with 0.5% Ocimene

| | No. of Lesions on | | Average No. of lesions | | |
|---|---|---|---|---|---|
| S.No. | Test | Control | Test | Control | % inhibition |
| 1 | 66 | 228 | 6.6 | 22.8 | 71.05 |
| 2. | 70 | 215 | 7.0 | 21.5 | 63.50 |
| 3. | 65 | 233 | 6.5 | 23.3 | 72.1 |

TABLE 5b

Treatment of CaRSV with 0.5% Ocimene

| | No. of Lesions on | | Average No. of lesions | | |
|---|---|---|---|---|---|
| S.No. | Test | Control | Test | Control | % inhibition |
| 1 | 60 | 198 | 6.0 | 19.8 | 69.6 |
| 2. | 65 | 195 | 6.5 | 19.5 | 66.6 |
| 3. | 58 | 180 | 5.8 | 18.0 | 67.7 |

TABLE 6a

Treatment of CaVMV with 2.5% Ocimene

| | No. of Lesions on | | Average No. of lesions | | |
|---|---|---|---|---|---|
| S.No. | Test | Control | Test | Control | % inhibition |
| 1 | 43 | 262 | 4.3 | 26.8 | 83.58 |
| 2. | 40 | 250 | 4.0 | 25.0 | 84.00 |
| 3. | 38 | 265 | 3.8 | 26.5 | 85.66 |

TABLE 6b

Treatment of CaRSV with 2.5% Ocimene

| | No. of Lesions on | | Average No. of lesions | | |
|---|---|---|---|---|---|
| S.No. | Test | Control | Test | Control | % inhibition |
| 1 | 40 | 205 | 4.0 | 20.5 | 80.4 |
| 2. | 25 | 135 | 2.5 | 13.5 | 81.4 |
| 3. | 35 | 185 | 3.5 | 18.5 | 81.0 |

When these pure isolated compounds were stored at 0° C. for two months, following results were obtained.

TABLE 7a

Treatment of CaVMV with DHT (stored at 0° C. for two months)

| | 0.5% concentration | | 2.5% concentration | |
|---|---|---|---|---|
| S. No. | Test | Control | Test | Control |
| 1 | 0 | 158 | 0 | 200 |
| 2. | 0 | 170 | 0 | 185 |
| 3. | 0 | 165 | 0 | 189 |

TABLE 7b

Treatment of CaRSV with DHT (stored at 0° C. for two months)

| | 0.5% concentration | | 2.5% concentration | |
|---|---|---|---|---|
| S. No. | Test | Control | Test | Control |
| 1 | 0 | 141 | 0 | 195 |
| 2. | 0 | 168 | 0 | 188 |
| 3. | 0 | 166 | 0 | 190 |

TABLE 8a

Treatment of CaVMV with Ocimene (stored at 0° C. for two months)

| | 0.5% concentration | | 2.5% concentration | |
|---|---|---|---|---|
| S. No. | Test | Control | Test | Control |
| 1 | 0 | 200 | 0 | 262 |
| 2. | 0 | 250 | 0 | 285 |
| 3. | 0 | 260 | 0 | 203 |

TABLE 8b

Treatment of CaRSV with Ocimene (stored at 0° C. for two months)

| | 0.5% concentration | | 2.5% concentration | |
|---|---|---|---|---|
| S. No. | Test | Control | Test | Control |
| 1 | 0 | 210 | 0 | 267 |
| 2. | 0 | 235 | 0 | 282 |
| 3. | 0 | 216 | 0 | 213 |

TABLE 9a

Percentage Inhibition of CaVMV with Three Treatments

| | 1st Treatment | | | IInd Treatment | | IIIrd Treatment | |
|---|---|---|---|---|---|---|---|
| Component | 0.5% | 2.5% | Component | 0.5% | 2.5% | 0.5% | 2.5% |
| Whole oil | 93.8 | 88.5 | Ocimene | 70.2 | 84.3 | 100 | 100 |
| | | | Dihydrotegetone | 72.2 | 83.6 | 100 | 100 |

I Treatment: With Whole oil
II Treatment: With Both the compounds after Extraction
III Treatment: With both the compounds after storing at 0° C.

TABLE 9b

Percentage Inhibition of CaRSV with Three Treatments

| | 1st Treatment | | | IInd Treatment | | IIIrd Treatment | |
|---|---|---|---|---|---|---|---|
| Component | 0.5% | 2.5% | Component | 0.5% | 2.5% | 0.5% | 2.5% |
| Whole oil | 91.5 | 87.5 | Ocimene | 67.9 | 80.9 | 100 | 100 |
| | | | Dihydrotegetone | 71.6 | 81.06 | 100 | 100 |

I Treatment: With Whole oil
II Treatment: With Both the compounds after Extraction
III Treatment: With both the compounds after storing at 0° C.

The main advantages of the present invention are:
1. *Tagetes minuta* plant grows wild in the hilly areas like Himachal Pradesh, Jammu and Kashmir, Uttar Pradesh, North Eastern States of India, and cultivated as commercial Tagetes oil crop hence easily available in bulk quality.
2. The oil and pure isolates are natural products and hence no threat to environment.
3. Application of oil and pure isolates ensure quick and efficient recovery from viral infections.
4. It also helps in the plant virus management.
5. Tagetes crop grows wild and can be distilled in rich pockets/places with prototype distillation unit.
6. A cheap, eco-friendly and easily available anti-viral natural product.

We claim:

1. A method for treating a plant infected with a plant virus comprising administering an antiviral composition comprising an effective amount of *Tagetes minuta* oil, Z-β-ocimene, dihydrotagetone and mixtures thereof to the plant infected with the plant virus.

2. The method as claimed in claim 1, wherein the effective amount is in the range of 0.5 to 2.5% by volume of the antiviral composition.

3. The method as claimed in claim 1, wherein the plant virus is selected from growth poty and diantho viruses.

4. The method as claimed in claim 1, wherein the plant is *Chenopodium amaranticolor*.

5. The method as claimed in claim 4, wherein the leaves of *Chenopodium amaranticolor* are infected with the plant virus.

6. The method as claimed in claim 3, wherein the growth poty virus is Carnation Vein Mottle (CaVMV) virus.

7. The method as claimed in claim 3, wherein the dianto virus is Carnation Ring Spot (CaRSV) virus.

8. A method for inhibiting a plant virus comprising administering an antiviral composition comprising an effective amount of *Tagetes minuta* oil, Z-β-ocimene, dihydrotagetone and mixtures thereof to a plant.

9. The method as claimed in claim 8, wherein the effective amount is in the range of 0.5 to 2.5% by volume of the antiviral composition.

10. The method as claimed in claim 8, wherein the plant virus is selected from growth poty and diantho viruses.

11. The method as claimed in claim 8, wherein the plant is *Chenopodium amaranticolor*.

12. The method as claimed in claim 11, wherein the leaves of *Chenopodium amaranticolor* are infected with the plant virus.

13. The method as claimed in claim 10, wherein the growth poty virus is Carnation Vein Mottle (CaVMV) virus.

14. The method as claimed in claim 10, wherein the dianto virus is Carnation Ring Spot (CaRSV) virus.

* * * * *